United States Patent
Kim et al.

(10) Patent No.: US 9,458,062 B2
(45) Date of Patent: Oct. 4, 2016

(54) METHOD OF MANUFACTURING CERAMIC PRIMARY CROWN AND CERAMIC PRIMARY CROWN MANUFACTURED BY THE SAME

(75) Inventors: Yong-Su Kim, Busan (KR); Hyun-Jun Jeon, Busan (KR); Kyung Sik Oh, Incheon (KR); Sung Ki Kim, Busan (KR); Se-Hoon Kim, Gyeonggi-do (KR); Joon Hyung Kim, Gyeonggi-do (KR); Young Pyo Hong, Gangwon-do (KR)

(73) Assignee: HASS CO., LTD., Gangwon-do (KR)

( * ) Notice: Subject to any disclaimer, the term of this patent is extended or adjusted under 35 U.S.C. 154(b) by 815 days.

(21) Appl. No.: 13/503,440

(22) PCT Filed: Dec. 14, 2010

(86) PCT No.: PCT/KR2010/008914
§ 371 (c)(1),
(2), (4) Date: Apr. 23, 2012

(87) PCT Pub. No.: WO2011/126200
PCT Pub. Date: Oct. 13, 2011

(65) Prior Publication Data
US 2013/0017514 A1  Jan. 17, 2013

(30) Foreign Application Priority Data
Apr. 6, 2010  (KR) ................ 10-2010-0031516

(51) Int. Cl.
*A61C 13/08* (2006.01)
*C04B 35/117* (2006.01)
(Continued)

(52) U.S. Cl.
CPC ........... *C04B 35/117* (2013.01); *A61C 13/083* (2013.01); *C04B 35/488* (2013.01);
(Continued)

(58) Field of Classification Search
CPC .................................................. C04B 35/117
See application file for complete search history.

(56) References Cited

U.S. PATENT DOCUMENTS 2,549,180 A * 4/1951 De Ment .................... 106/35
4,197,118 A * 4/1980 Wiech, Jr. .................. 75/228
(Continued)

FOREIGN PATENT DOCUMENTS

CN       1489987 A    4/2004
JP    2000-139953 A   5/2000
(Continued)

OTHER PUBLICATIONS

International Search Report for related international application No. PCT/KR2010/008914, report dated Aug. 18, 2011.
(Continued)

*Primary Examiner* — Galen Hauth
(74) *Attorney, Agent, or Firm* — Miller, Matthias & Hull LLP

(57) ABSTRACT

A method of manufacturing a ceramic primary crown including mixing a source material including zirconia or alumina that configures a frame of a primary crown, a polymer for reducing viscosity and applying ductility upon injection molding, and a toner for providing the same or similar color as baby teeth, heating the polymer contained in the mixed source material to have ductility, injection molding the heated source material, extracting the polymer to reduce brittleness and increase ductility with respect to the injection-molded matter, removing fat to completely eliminate the polymer element from the injection-molded matter, from which the polymer is partially extracted through the polymer extraction, sintering the fat-removed body, from which the polymer is removed, to improve mechanical properties, and polishing an outer surface of the sintered body to provide gloss, and performing barrel-finishing to remove a burr.

7 Claims, 2 Drawing Sheets

(51) Int. Cl.
  A61C 13/083     (2006.01)
  C04B 35/488    (2006.01)
  C04B 35/626    (2006.01)
  C04B 35/632    (2006.01)
  C04B 35/634    (2006.01)
  C04B 35/638    (2006.01)
  A61C 13/20     (2006.01)
  B28B 1/24      (2006.01)

(52) U.S. Cl.
  CPC ....... C04B35/6261 (2013.01); C04B 35/6264 (2013.01); C04B 35/632 (2013.01); C04B 35/638 (2013.01); C04B 35/63408 (2013.01); C04B 35/63416 (2013.01); A61C 13/081 (2013.01); A61C 13/206 (2013.01); B28B 1/24 (2013.01); C04B 2235/3232 (2013.01); C04B 2235/3272 (2013.01); C04B 2235/6022 (2013.01); C04B 2235/656 (2013.01); C04B 2235/6562 (2013.01); C04B 2235/6565 (2013.01); C04B 2235/6567 (2013.01); C04B 2235/9661 (2013.01)

(56) References Cited

U.S. PATENT DOCUMENTS

| | | | | |
|---|---|---|---|---|
| 5,417,756 | A * | 5/1995 | Bayer et al. | 106/272 |
| 5,877,232 | A * | 3/1999 | Storch | A61K 6/0017 433/228.1 |
| 5,984,683 | A * | 11/1999 | Sakata et al. | 433/218 |
| 6,488,503 | B1 * | 12/2002 | Lichkus et al. | 433/202.1 |
| 6,660,194 | B1 * | 12/2003 | Arita | 264/17 |
| 8,651,867 | B2 * | 2/2014 | Zilberman | 433/218 |
| 2002/0057981 | A1 * | 5/2002 | Park | B22F 3/02 419/8 |
| 2004/0138049 | A1 * | 7/2004 | Yasrebi | B22F 3/225 501/127 |
| 2004/0245663 | A1 * | 12/2004 | MacDougald et al. | 264/16 |

FOREIGN PATENT DOCUMENTS

| | | |
|---|---|---|
| JP | 2000139953 A | 5/2000 |
| JP | 2003-047622 A | 2/2003 |
| JP | 2003047622 A | 2/2003 |
| JP | 2007-244803 A | 9/2007 |
| JP | 2007244803 A | 9/2007 |
| JP | 2008-095726 A | 12/2008 |
| JP | 2008295726 A | 12/2008 |

OTHER PUBLICATIONS

Progress of Ceramic Injection Molding; Wang Xiu, Zie Zhipeng, Li Jianbao, Huang Yong; (Tsinghua University, Beijing 100084, China).

Research on the Coloration of Dental Zirconia; Lin Yongzhao, Wang Chen, Yi Yuanfu, Dong Limin, Zan Qingfeng, Tian Jiemo; (1. State Key Laboratory of New Ceramics and Fine Processing, Tsinghua University, Beijing 100084, China); (2. General Hospital of Armed Police Forces, Beijing 100039, China).

* cited by examiner

METHOD OF MANUFACTURING CERAMIC PRIMARY CROWN AND CERAMIC PRIMARY CROWN MANUFACTURED BY THE SAME

CROSS REFERENCE TO RELATED APPLICATIONS

This application is a 35 USC §371 US National Stage patent application of International Patent Application No. PCT/KR2010/008914 filed on Dec. 14, 2010, and claims priority to and the benefit of Korean Patent Application No. 10-2010-0031516, filed Apr. 6, 2010, the disclosure of which is incorporated herein by reference in its entirety.

BACKGROUND

1. Field of the Disclosure

This disclosure relates to a primary crown for children's prosthesis and a method of manufacturing the same, and more particularly, to a method of manufacturing a ceramic primary crown and a ceramic primary crown manufactured by the same, that are capable of improving aesthetic appreciation and bioaffinity using a source material such as zirconia or alumina having high strength and toughness, and enabling easy manufacture and mass production using injection molding to reduce manufacturing cost and product price, widely utilizing the primary crown for children's prosthesis.

2. Background of the Disclosure

In general, primary crown recovery for children's prosthesis is a medical procedure for recovering the crown of a baby tooth seriously damaged due to dental caries or injury.

If the primary crown recovery is not performed in a timely way, since neighboring teeth are pushed toward the place of a lost tooth so that a permanent tooth cannot surface through the place, a device or a recovery support should maintain the place until the permanent tooth protrudes from the place.

While a primary crown is made of metal and resin and has been used until now, strength and aesthetic appreciation cannot be simultaneously satisfied, and tone stability and strength are degraded to generate discoloration and cracks, resulting in a bad appearance of front teeth of the upper jaw, which are aesthetically important.

As economic affluence improves, procedures of adult implants rapidly increase. Interest in improvement of aesthetic appreciation also increases, and further, satisfaction and high standard of children's prosthesis procedures increase, which leads to an increase in demand, but the current domestic market of the primary crown mostly relies upon imports.

While there is a need to develop a ceramic primary crown having high strength, good aesthetic appreciation and improved biocompatibility in comparison with the conventional metal and resin type for primary crown recovery, no ceramic primary crown product reach a satisfactory level up to now.

A conventional ceramic, which is manufactured through a powder pressure forming process, generates pressure imbalance upon formation thereof and defects caused therefrom to require an additional precise machining step, generating excessive machining cost.

SUMMARY OF THE DISCLOSURE

In order to solve the problems, the this disclosure provides a method of manufacturing a ceramic primary crown and a ceramic primary crown manufactured by the same, that are capable of improving aesthetic appreciation and bioaffinity using a source material such as zirconia or alumina having high strength and toughness, and enabling easy manufacture and mass production using injection molding to reduce manufacturing cost and product price, widely utilizing the primary crown for children's prosthesis.

This disclosure is directed to a method of manufacturing a ceramic primary crown including: mixing a source material including zirconia or alumina that configures a frame of a primary crown, a polymer for reducing viscosity and applying ductility upon injection molding, and a toner for providing the same or similar color as baby teeth; heating the polymer contained in the mixed source material to have ductility; injection molding the heated source material; extracting the polymer to reduce brittleness and increase ductility of the injection-molded matter; removing fat to completely eliminate the polymer element from the injection-molded matter, from which the polymer is partially removed through the polymer extraction; sintering the fat-removed body, from which the polymer is removed, to improve mechanical properties; and polishing an outer surface of the sintered body to provide gloss, and performing barrel-finishing to remove a burr.

BRIEF DESCRIPTION OF THE DRAWINGS

The above and other objects, features and advantages of this disclosure will become more apparent to those of ordinary skill in the art by describing in detail example embodiments thereof with reference to the attached drawings, in which.

DETAILED DESCRIPTION OF THE DISCLOSURE

Figure 1:
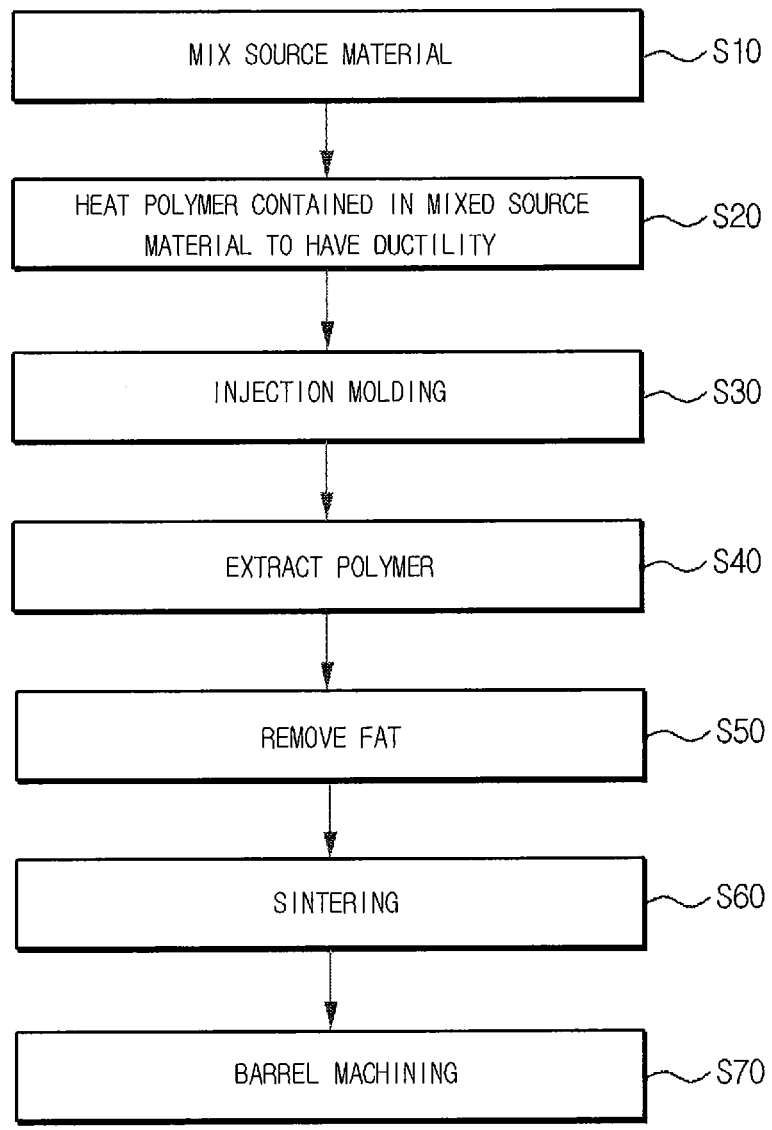
FIG. 1 is a view showing a process of manufacturing a ceramic primary crown in accordance with an exemplary embodiment of the present invention.

This disclosure provides a method of manufacturing a ceramic primary crown including: mixing a source material including zirconia or alumina that configures a frame of a primary crown, a polymer for reducing viscosity and applying ductility upon injection molding, and a toner for providing the same or similar color as baby teeth; heating the polymer contained in the mixed source material to have ductility; injection molding the heated source material; extracting the polymer to reduce brittleness and increase ductility with respect to the injection-molded matter; removing fat to completely eliminate the polymer element from the injection-molded matter, from which the polymer is partially extracted through the polymer extraction; sintering the fat-removed body, from which the polymer is removed, to improve mechanical properties; and polishing an outer surface of the sintered body to provide gloss, and performing barrel-finishing to remove a burr.

The zirconia ($ZrO_2$) or alumina ($Al_2O_3$) may be contained in an amount of 80 to 90 wt % with respect to the source material, the polymer may be contained in an amount of 9 to 19 wt % with respect to the source material, and the toner may be contained in an amount of 0.005 to 1 wt % with respect to the source material.

The polymer may include ethylene vinyl acetate, paraffin wax, low density polyethylene and stearic acid.

The ethylene vinyl acetate may be contained in an amount of 7 to 30 wt % with respect to the polymer, the paraffin wax may be contained in an amount of 50 to 65 wt % with respect to the polymer, the low density polyethylene may be contained in an amount of 15 to 35 wt % with respect to the polymer, and the stearic acid may be contained in an amount of 1 to 5 wt % with respect to the polymer.

The toner may be at least one inorganic material selected from titanium dioxide ($TiO_2$) representing white, red iron oxide ($Fe_2O_3$) and yellow iron oxide ($Fe_2O_3$).

Extracting the polymer may be performed by stirring the polymer in an extraction liquid at a temperature of 40 to 90° C. for 1 to 24 hours, and the extraction liquid may include acetone, N-methylpyrollidone, or a mixed solvent thereof.

Removing the fat may be constituted by a heat treatment process performed at a temperature of 800 to 1000° C. for 6 to 24 hours to burn and remove the polymer element remaining in the injection-molded matter.

The sintering may be constituted by a process of heat-treating the fat-removed body, from which the polymer is removed, at a temperature of 1200 to 1550° C. for 6 to 48 hours.

The fat removal and the sintering may be continuously performed in one furnace.

In addition, the present invention provides a ceramic primary crown for children's prosthesis manufactured using the method of manufacturing a ceramic primary crown.

Example Embodiments

Hereinafter, an example embodiment of this disclosure will be described in detail with reference to the accompanying drawings. However, this disclosure is not limited to the embodiments disclosed below, but can be implemented in various forms. The following embodiments are described in order to enable those of ordinary skill in the art to embody and practice the concepts and techniques disclosed herein present invention.

This disclosure provides a ceramic primary crown for children's prosthesis and a method of manufacturing the same that are capable of simultaneously satisfying aesthetic appreciation and strength, enabling mass production, improving quality stability of products, and enabling easy manufacture using injection molding.

FIG. 1 is a view showing a process of manufacturing a ceramic primary crown in accordance with an exemplary embodiment of this disclosure.

A method of manufacturing a ceramic primary crown in accordance with an exemplary embodiment of this disclosure includes mixing a source material including zirconia or alumina that configures a frame of a primary crown, a polymer for reducing viscosity and applying ductility upon injection molding, and a toner for providing the same or similar color as baby teeth (S10); heating the polymer contained in the mixed source material to have ductility (S20); injection molding the heated source material (S30); extracting the polymer to reduce brittleness and increase ductility with respect to the injection-molded matter (S40); removing fat to completely eliminate the polymer element from the injection-molded matter, from which the polymer is partially extracted through the polymer extraction (S50); sintering the fat-removed body, from which the polymer is removed, to improve mechanical properties (S60); and polishing an outer surface of the sintered body to provide gloss, and performing barrel-finishing to remove a burr (S70).

Hereinafter, the method of manufacturing the ceramic primary crown will be described in detail.

First, a polymer of 9 to 19 wt %, which is a solvent element to provide viscosity upon an injection molding process, zirconia ($ZrO_2$) or alumina ($Al_2O_3$) of 80 to 90 wt %, and a toner of 0.005 to 1 wt % for colorizing are mixed.

The polymer includes ethylene vinyl acetate (EVA), paraffin wax, low density polyethylene (LDPE) and stearic acid. The EVA may be contained in an amount of 7 to 30 wt % with respect to the polymer, the paraffin wax may be contained in an amount of 50 to 65 wt % with respect to the polymer, the LDPE may be contained in an amount of 15 to 35 wt % with respect to the polymer, and the stearic acid may be contained in an amount of 1 to 5 wt % with respect to the polymer.

The toner is to provide the same or similar color as baby teeth, and may use titanium dioxide ($TiO_2$), which is an inorganic toner representing white, red iron oxide ($Fe_2O_3$), yellow iron oxide ($Fe_2O_3$), or a mixture thereof. When the red iron oxide or yellow iron oxide is mixed with zirconia or alumina and then sintered, the red iron oxide or yellow iron oxide represents a thin yellow similar to the color of baby teeth. The titanium dioxide represents white to provide a color very similar to the color of baby teeth.

After the mixing process, a pulverization process may be performed for size uniformity and miniaturization of particles of the source material. The pulverization may include a wet ball milling process. Specifically describing the ball milling process, the source material such as the zirconia or alumina, polymer and toner are loaded into a ball milling machine to be mixed with a solvent such as water or alcohol, and the ball milling machine is rotated at a certain speed to mechanically pulverize and uniformly mix the source material particles. Balls used in ball milling may be formed of ceramics such as zirconia or alumina, and the balls may have the same size or two or more different sizes. The size of the balls, milling time, revolutions per minute (rpm) of the ball milling machine, etc., are adjusted to perform pulverization to a target particle size. For example, in consideration of the particle size, the size of the balls may be set to a range of 1 mm to 30 mm, and the ball milling machine may be set to a range of 50 to 500 rpm. The ball milling is performed for 1 to 48 hours in consideration of the target particle size, etc. The source material is pulverized into fine particles by the ball milling to have uniform size distribution of spherical particles.

When mixing is performed, the source material is heated at a temperature of 100 to 180° C. for 1 to 12 hours. Moisture (elements such as water, alcohol, etc., used as a solvent in the wet ball milling process) contained in the pulverized source material is removed by the heating, and viscosity of the polymer is lowered to have ductility, facilitating the injection molding process.

The heated source material is inserted into the injection molding machine to perform the injection molding process. Since the injection molding process is well known in the art, a detailed description thereof will be omitted. An injection temperature upon the injection molding may be 130 to 160° C. The injection-molded matter passed through the injection molding process has strong brittleness, which requires careful handling thereof. Accordingly, in order to improve smooth machining and product quality, a process of reducing brittleness and increasing ductility with respect to the injection-molded matter is needed.

A polymer extraction process is performed on the injection-molded matter to reduce brittleness and increase ductility. The polymer extraction process, which is a process of reducing brittleness and increasing ductility of the injection-molded matter, stirs the matter in an extraction liquid (a solvent) at a temperature of 40 to 90° C. for 1 to 24 hours, preferably 6 to 12 hours, and partially extracts the polymer (a solvent element material). Some of the EVA, paraffin wax, LDPE and stearic acid contained in the polymer may be extracted and removed by the polymer extraction process. The extraction liquid may include a solvent such as acetone, N-methylpyrollidone, or a mixture thereof that can dissolve the EVA, paraffin wax, LDPE and stearic acid.

The injection-molded matter, from which the polymer is partially extracted by the polymer extraction process, may have low brittleness and very high ductility in comparison with an injection molded body just after the injection molding, increasing probability of deformation of products upon the handling thereof.

In order to completely remove the polymer element from the injection-molded matter, from which the polymer is partially extracted by the polymer extraction process, a fat removal process is performed. The fat removal process includes a heat treatment process of completely removing the polymer element remaining in the injection-molded matter at a temperature of 800 to 1000° C., preferably 850 to 950° C. for 6 to 24 hours. If not passing the fat removal process, the polymer element remaining in the injection-molded matter may cause bubbles during the following sintering process to deteriorate mechanical properties of a sintered body, generating voids or fine cracks in the sintered body.

After the fat removal process, the fat-removed body, from which the polymer is removed, is sintered. The sintering process, which is a process of improving mechanical properties, includes a process of heat-treating the fat-removed body, from which the polymer is removed, at a temperature of 1200 to 1550° C. for 6 to 48 hours.

The fat removal process and the sintering process can secure process efficiency under a condition that the processes are continuously performed in one furnace as described above.

Figure 2:
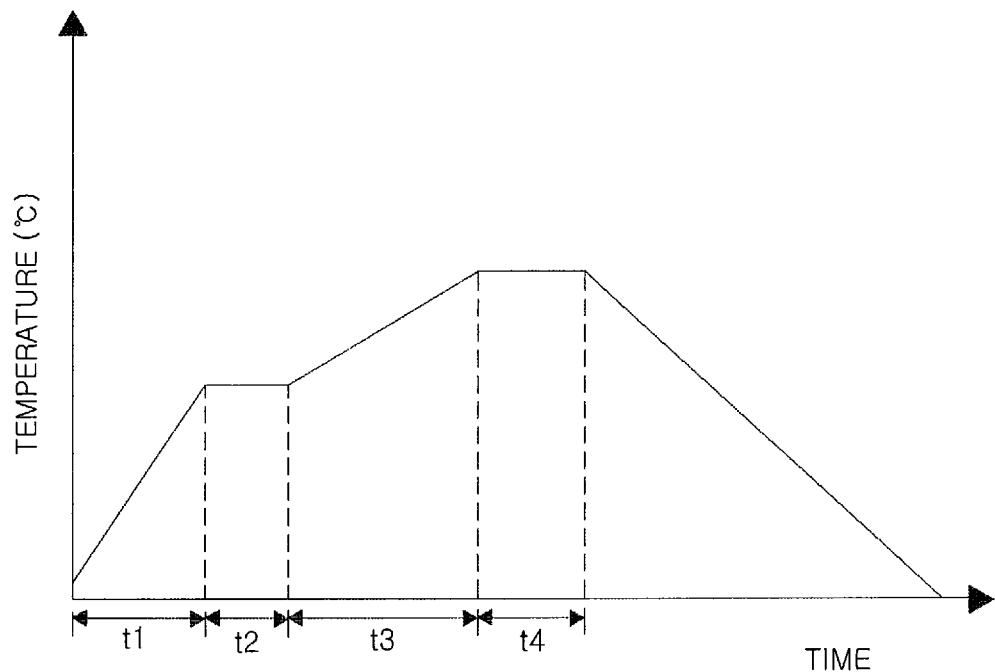
FIG. 2 is a view for explaining a process of performing a fat removal process and a sintering process in one furnace in-situ.

Hereinafter, the fat removal process and the sintering process will be described in detail. FIG. 2 is a view for explaining the fat removal process and the sintering process, which are performed on one furnace in-situ.

Referring to FIG. 2, the injection-molded matter, from which the solvent is extracted, is loaded into the furnace. The furnace is increased to a temperature of 800 to 1000° C., which is higher than the temperature at which the polymer is burnt and lower than a sintering temperature, using a heating unit installed at the furnace (a t1 section of FIG. 2). Here, temperature-increasing speed may be 5 to 50° C./min. When the temperature-increasing speed exceeds 50° C./min, a thermal stress may be applied to the injection-molded matter due to abrupt variation in temperature, and when less than 5° C./min, a long time is required to decrease productivity.

When the temperature of the furnace arrives at a temperature of 800 to 1000° C., the temperature is maintained for 6 to 24 hours (a t2 section of FIG. 2) to burn and remove the polymer. The polymer element such as the EVA, paraffin wax, LDPE) or stearic acid, remaining in the injection-molded matter, from which the solvent is extracted, is burnt or evaporated at a temperature of about 800 to 1000° C. to be completely removed. As described above, the polymer element present in the injection-molded matter can be easily removed from the injection-molded matter through the fat removal process.

After the fat removal process is performed, the temperature of the furnace is increased to a target sintering temperature of 1200 to 1550° C. (a t3 section of FIG. 2). Here, temperature-increasing speed may be 5 to 50° C./min. When the temperature-increasing speed exceeds 50° C./min, a thermal stress may be applied to the fat-removed body due to abrupt variation in temperature, and when less than 5° C./min, a long time is required to decrease productivity.

When the temperature of the furnace arrives at the sintering temperature of 1200 to 1550° C., the temperature is maintained for 6 to 24 hours to perform the sintering (a t4 section of FIG. 2). The sintering temperature may be 1200 to 1550° C. in consideration of diffusion of the particles and necking between the particles. When the sintering temperature is too high, excessive growth of the particles may degrade mechanical properties, and when the sintering temperature is too low, imperfect sintering may degrade characteristics of the sintered body, so that sintering may be performed in the above sintering temperature range. A fine structure, particle size, etc., of the sintered body are different according to the sintering temperature. When the sintering temperature is low, surface diffusion is dominant, whereas, when the sintering temperature is high, both lattice diffusion and grain boundary diffusion are preformed. The sintering time may be 6 to 24 hours. When the sintering time is too long, energy consumption is increased to be uneconomical and a sintering effect can no longer be counted on, and when the sintering time is short, imperfect sintering may degrade characteristics of the sintered body.

The furnace is cooled and the sintered body is unloaded. The furnace may be cooled in a natural state by cutting the electric power of the heating unit, or cooled by arbitrarily setting a temperature-decreasing rate (for example, 10° C./min).

An outer surface of the sintered body passed through the sintering process is polished to provide gloss, and barrel finishing is performed to remove a fine burr. The barrel finishing process may be performed using a barrel polishing apparatus.

As described above, the ceramic primary crown manufactured by this disclosure is generally formed of ceramic different from the conventional metal and resin primary crown to have good aesthetic appreciation and high bioaffinity, and zirconia or alumina having high strength and toughness is used as the source material to improve aesthetic appreciation and increase bioaffinity to be widely applied for industrialization of medical materials.

As can be seen from the foregoing, since the ceramic primary crown manufactured in accordance with this disclosure is generally formed of ceramic different from the conventional metal and resin primary crown, aesthetic appreciation is improved and bioaffinity is increased. In addition, since zirconia or alumina having high strength and toughness is used as the source material, good aesthetic appreciation and high bioaffinity increase applicability for industrialization of medical materials.

According to this disclosure, while zirconia or alumina having bad machinability but high strength and toughness is used as a material, since easy manufacture and mass production through the injection molding becomes possible, the zirconia and alumina can be widely used for the primary crown for children's prosthesis due to reduction in manufacturing cost and low price.

While this disclosure shows and describes certain example embodiments, it will be understood by those skilled in the art that various changes in form and details may be made therein without departing from the spirit and scope of this disclosure as defined by the appended claims.

What is claimed is:

1. A method of manufacturing a ceramic primary crown comprising:
   mixing a source material including zirconia or alumina that configures a frame of a primary crown, a polymer for reducing viscosity and applying ductility upon injection molding, and a toner for providing the same or similar color as baby teeth;
   pulverizing the source material for size uniformity and miniaturization of particles of the source material;
   heating the polymer contained in the mixed source material to have ductility;
   injection molding the heated source material to form a body;
   at least partially extracting the polymer from the body to reduce brittleness and increase ductility of the body;
   completely removing the polymer from the body;
   sintering the body to form a sintered body; and
   polishing an outer surface of the sintered body to provide gloss and performing barrel-finishing to remove a burr,
   wherein the toner comprises at least one inorganic material selected from red iron oxide ($Fe_2O_3$) and yellow iron oxide ($Fe_2O_3$),
   wherein pulverizing the source material includes a ball milling process which balls used in ball milling are formed of zirconia or alumina,
   wherein the complete removing of the polymer is performed at a temperature ranging from 100 to 180° C. for 1 to 12 hours,
   wherein at least partially extracting the polymer comprises stirring the polymer in an extraction liquid at a temperature ranging from 40 to 90° C. for 1 to 24 hours to extract the polymer, and the extraction liquid comprises N-methylpyrollidone.

2. The method according to claim 1, wherein the zirconia or alumina is contained in an amount of 80 to 90 wt % with respect to the source material, the polymer is contained in an amount of 9 to 19 wt % with respect to the source material, and the toner is contained in an amount of 0.005 to 1 wt % with respect to the source material.

3. The method according to claim 1, wherein the polymer comprises ethylene vinyl acetate, paraffin wax, low density polyethylene and stearic acid.

4. The method according to claim 3, wherein the ethylene vinyl acetate is contained in an amount of 7 to 30 wt % with respect to the polymer, the paraffin wax is contained in an amount of 50 to 65 wt % with respect to the polymer, the low density polyethylene is contained in an amount of 15 to 35 wt % with respect to the polymer, and the stearic acid is contained in an amount of 1 to 5 wt % with respect to the polymer.

5. The method according to claim 1, wherein removing the polymer comprises a heat treatment process performed at a temperature of 800 to 1000° C. for 6 to 24 hours to burn and remove the polymer remaining in the injection-molded matter.

6. The method according to claim 1, wherein the sintering comprises a process of heat-treating the body, from which the polymer is removed, at a temperature of 1200 to 1550° C. for 6 to 48 hours.

7. The method according to claim 1, wherein the fat removal of the polymer and the sintering are continuously performed in one furnace.

* * * * *